United States Patent
McCarthy

(10) Patent No.: US 9,700,435 B2
(45) Date of Patent: Jul. 11, 2017

(54) SURGICAL DELIVERY SYSTEM AND METHOD

(71) Applicant: Warsaw Orthopedic, Inc., Warsaw, IN (US)

(72) Inventor: Kevin Patrick McCarthy, Prairieville, LA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 599 days.

(21) Appl. No.: 13/829,222

(22) Filed: Mar. 14, 2013

(65) Prior Publication Data
US 2014/0277459 A1  Sep. 18, 2014

(51) Int. Cl.
*A61F 2/46* (2006.01)
*A61B 17/70* (2006.01)
*A61F 2/44* (2006.01)

(52) U.S. Cl.
CPC .......... *A61F 2/4611* (2013.01); *A61B 17/707* (2013.01); *A61B 17/7097* (2013.01); *A61F 2/4455* (2013.01)

(58) Field of Classification Search
CPC .... A61F 2/4611; A61F 2/4455; A61F 2/4405; A61B 17/707
See application file for complete search history.

(56) References Cited

U.S. PATENT DOCUMENTS

| | | | |
|---|---|---|---|
| 2,621,655 A * | 12/1952 | Olson | A61D 7/00 221/232 |
| 3,402,712 A * | 9/1968 | Eisenhand | A61M 37/0069 221/19 |
| 4,700,692 A * | 10/1987 | Baumgartner | A61M 37/0069 600/7 |
| 4,995,867 A * | 2/1991 | Zollinger | A61M 31/00 222/388 |
| 5,741,261 A | 4/1998 | Moskovitz et al. | |
| 6,220,479 B1 * | 4/2001 | Fishman | B65D 83/0409 221/24 |
| 6,500,206 B1 | 12/2002 | Bryan | |
| 6,730,095 B2 * | 5/2004 | Olson, Jr. | A61B 17/7098 604/218 |
| 7,651,496 B2 | 1/2010 | Keegan et al. | |
| 7,780,709 B2 | 8/2010 | Bruneau et al. | |
| 7,789,898 B2 | 9/2010 | Peterman | |
| 8,092,464 B2 * | 1/2012 | McKay | A61B 17/7044 604/218 |
| 8,505,771 B2 * | 8/2013 | Read | A63B 47/002 221/260 |
| 2004/0111053 A1 * | 6/2004 | Nicolette | A61M 37/0069 604/59 |

(Continued)

FOREIGN PATENT DOCUMENTS

WO  WO 2007044705 A2 *  4/2007  .......... A61B 17/025

*Primary Examiner* — Zade Coley

(57) ABSTRACT

An implant delivery device includes a body having a first portion and a second transverse portion. The second transverse portion defines a cavity in at least a portion thereof. A first member has at least a portion thereof disposable in the cavity and movable relative to the second portion. A second member has a surface disposed about an implant disposable in the cavity. The surface of the second member includes an opening. The first member is engageable with the implant to expel the implant from the cavity and through the opening. Methods of use are disclosed.

14 Claims, 8 Drawing Sheets

(56) References Cited

U.S. PATENT DOCUMENTS

| | | | |
|---|---|---|---|
| 2005/0131409 A1 | 6/2005 | Chervitz et al. | |
| 2005/0131422 A1 | 6/2005 | Anderson et al. | |
| 2005/0154389 A1 | 7/2005 | Selover et al. | |
| 2005/0159746 A1 | 7/2005 | Grob et al. | |
| 2005/0261681 A9* | 11/2005 | Branch | A61B 17/1671 600/201 |
| 2006/0058791 A1 | 3/2006 | Broman et al. | |
| 2006/0167454 A1 | 7/2006 | Ludwig et al. | |
| 2006/0217718 A1 | 9/2006 | Chervitz et al. | |
| 2006/0229612 A1 | 10/2006 | Rothman et al. | |
| 2006/0235387 A1 | 10/2006 | Peterman | |
| 2006/0247623 A1 | 11/2006 | Anderson et al. | |
| 2006/0276790 A1 | 12/2006 | Dawson et al. | |
| 2007/0060941 A1* | 3/2007 | Reiley | A61B 10/025 606/192 |
| 2007/0173832 A1 | 7/2007 | Tebbe et al. | |
| 2007/0186923 A1* | 8/2007 | Poutiatine | A61J 7/0038 128/200.14 |
| 2007/0270808 A1 | 11/2007 | Drewry et al. | |
| 2007/0270844 A1 | 11/2007 | Lin et al. | |
| 2008/0103505 A1 | 5/2008 | Fransen | |
| 2008/0154367 A1 | 6/2008 | Justis et al. | |
| 2008/0154374 A1 | 6/2008 | Labrom | |
| 2009/0118831 A1 | 5/2009 | Trieu | |
| 2009/0138044 A1 | 5/2009 | Bergeron et al. | |
| 2009/0157087 A1* | 6/2009 | Wei | A61B 17/7097 606/99 |
| 2009/0192474 A1 | 7/2009 | Wei et al. | |
| 2009/0234277 A1 | 9/2009 | Wei et al. | |
| 2009/0292361 A1* | 11/2009 | Lopez | A61F 2/446 623/17.15 |
| 2010/0036419 A1 | 2/2010 | Patel et al. | |
| 2010/0100133 A1 | 4/2010 | Carl et al. | |
| 2010/0106194 A1 | 4/2010 | Bonutti et al. | |
| 2010/0114317 A1* | 5/2010 | Lambrecht | A61B 17/70 623/17.11 |
| 2010/0137915 A1 | 6/2010 | Anderson et al. | |
| 2010/0152779 A1 | 6/2010 | Allard et al. | |
| 2010/0174321 A1 | 7/2010 | Schaller | |
| 2010/0203155 A1 | 8/2010 | Wei et al. | |
| 2010/0204699 A1 | 8/2010 | Wei et al. | |
| 2010/0217326 A1 | 8/2010 | Bowden et al. | |
| 2010/0222823 A1 | 9/2010 | Bowden et al. | |
| 2010/0268232 A1* | 10/2010 | Betz | A61F 2/4603 606/79 |
| 2010/0280555 A1 | 11/2010 | Aflatoon et al. | |
| 2010/0312279 A1 | 12/2010 | Gephardt et al. | |
| 2011/0022091 A1 | 1/2011 | Anderson et al. | |
| 2013/0190769 A1* | 7/2013 | Morgenstern Lopez | A61B 17/1757 606/90 |

* cited by examiner

SURGICAL DELIVERY SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Fusion and fixation treatments may employ implants for posterolateral fusion to achieve arthrodesis. This disclosure describes an improvement over these prior art technologies.

SUMMARY OF THE INVENTION

Accordingly, a surgical system is provided for implant delivery to a surgical site and a method for treating a spine. It is contemplated that the surgical system and method may be employed for an arthrodesis treatment. It is further contemplated that the surgical system and method may be employed for a posterolateral fusion using minimally invasive and percutaneous techniques.

In one particular embodiment, in accordance with the principles of the present disclosure, an implant delivery device is provided. The implant delivery device includes a body having a first portion and a second transverse portion. The second transverse portion defines a cavity in at least a portion thereof. A first member has at least a portion thereof disposable in the cavity and movable relative to the second portion. A second member has a surface disposed about an implant disposable in the cavity. The surface of the second member includes an opening. The first member is engageable with the implant to expel the implant from the cavity and through the opening.

In one embodiment, an implant delivery system is provided. The implant delivery system includes a body extending from a proximal end to a distal end along a longitudinal axis of the body. The proximal end includes a handle and an elongated channel that extend transversely from the distal end. The channel defines an open distal face. A rod is movable relative to the body. The rod includes an axial portion disposed with the handle and a transverse portion disposable with the channel. An implant is disposable in the channel. A covering that defines a surface is disposable about at least a portion of the implant disposed in the channel. The surface of the covering is configured to form an opening. The rod is engageable with the implant in the channel to expel the implant from the channel through the opening.

In one embodiment, a method for treating a spine is provided. The method includes the steps of: providing a delivery device including: a body having a first portion, a second transverse portion and defining a cavity in at least a portion thereof, a first member having at least a portion thereof disposable in the cavity, and a second member disposable with the second portion and having a surface including an opening; providing an implant; disposing at least a portion of the implant in the cavity; disposing the second member about at least a portion of the implant in a configuration to support the implant with the second portion; disposing the second portion adjacent a portion of the spine; and actuating the first member to engage the implant in a configuration to expel the implant from the cavity through the opening and adjacent the portion of the spine.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
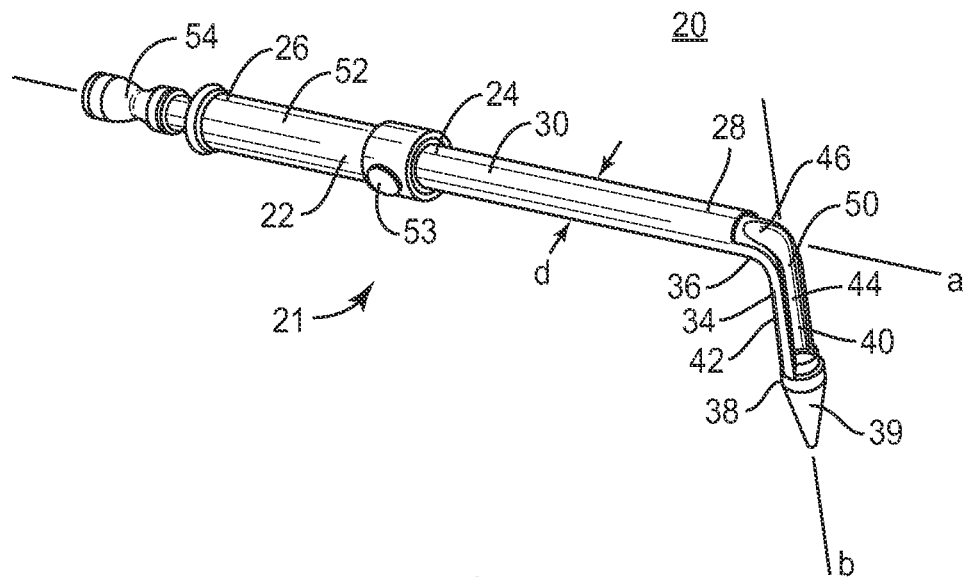
FIG. 1 is a perspective view of one particular embodiment of an implant delivery device of a system in accordance with the principles of the present disclosure.
Figure 2:
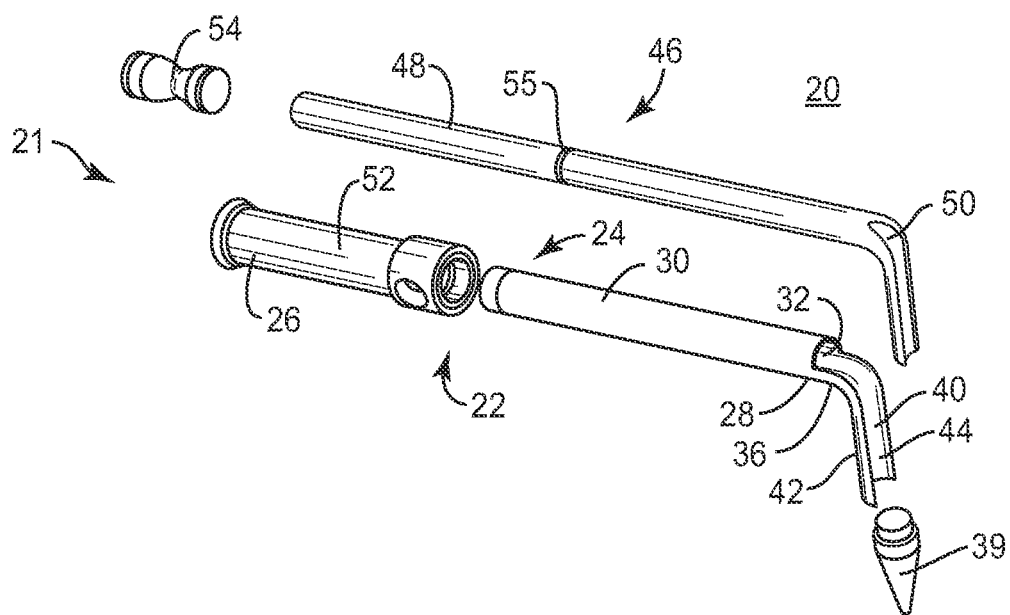
FIG. 2 is a perspective view of the implant delivery device shown in FIG. 1 with parts separated.
Figure 3:
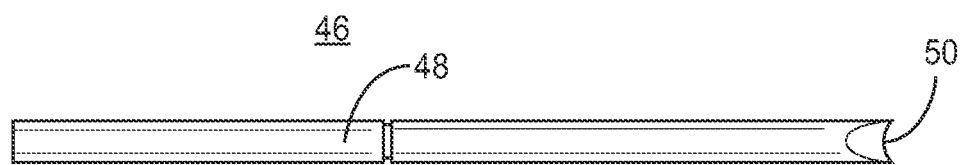
FIG. 3 is a side view of a rod of the implant delivery device shown in FIG. 1.
Figure 4:
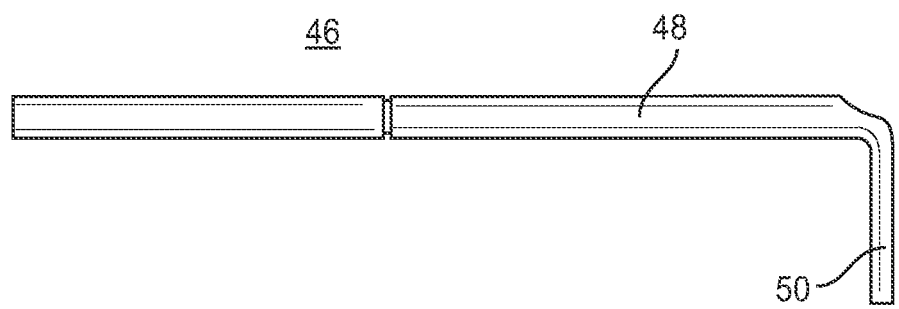
FIG. 4 is a side view of the rod shown in FIG. 3.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical system and methods of use disclosed can be employed to obtain a posterolateral fusion through a minimally invasive or percutaneous technique. It is further envisioned that the disclosed system and methods can be used in connection with and/or to supplement an instrumented minimally invasive or percutaneous interbody fusion. In one embodiment, the surgical system and methods of use disclosed are designed to avoid undesirable engagement or interference with soft tissue. In one embodiment, one or all of the components of the surgical system are disposable, peel-pack, pre-packed sterile devices used with an implant. The device may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which is illustrated in the accompanying figures. Turning now to FIGS. 1-4, there is illustrated components of a surgical system, such as, for example, an implant delivery system 20 in accordance with the principles of the present disclosure.

The components of implant delivery system 20 can be fabricated from biologically acceptable materials suitable for medical applications, including metals, synthetic polymers, ceramics and bone material and/or their composites, depending on the particular application and/or preference of a medical practitioner. For example, the components of system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyamide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening elements and/or instruments, as described herein.

Figure 8:
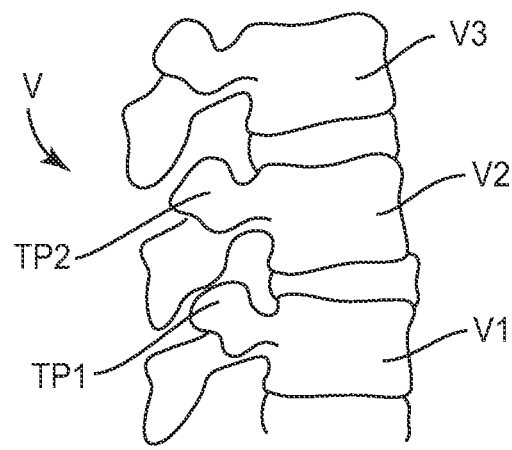
FIG. 8 is a perspective view of a section of a spine.

Implant delivery system 20 is employed, for example, with a minimally invasive or percutaneous technique to deliver an implant to a surgical site within a body of a patient, for example, a section of a spine (FIG. 8). In one embodiment, the components of implant delivery system 20 are configured to position the implant with the transverse process(es) of the spine to achieve a posterolateral fusion for treatment while avoiding undesired engagement with adjacent soft tissues.

Implant delivery system 20 includes an implant delivery device 21. Implant delivery device 21 includes a body 22 having a first portion 24 that extends from a proximal end 26 to a distal end 28 along a longitudinal axis a of body 22. Body 22 is configured for disposal within a body cavity to deliver an implant to a surgical site, as will be described. Body 22 has a smooth or even outer surface 30 and a cylindrical cross-section. It is envisioned that all or only a portion of the outer surface of body 22 may have alternate surface configurations, such as, for example, rough, threaded for connection with other instruments, arcuate, undulating, porous, semi-porous, dimpled, polished and/or textured according to the requirements of a particular application. It is contemplated that body 22 may have alternate cross section configurations, such as, for example, oval, oblong, triangular, rectangular, square, polygonal, irregular, uniform, non-uniform, variable and/or tapered. It is further contemplated that body 22 may include fastening elements such as anchors, detents and/or openings for connection to surgical instruments.

Body 22 has an inner diameter that defines an inner cavity, such as, for example, a passageway 32 and an outer diameter d, which is generally uniform. It is contemplated that the thickness defined by the inner diameter and diameter d may be uniformly increasing or decreasing, or have alternate diameter dimensions along longitudinal axis a. It is further contemplated that diameter d may be in a range of approximately 0.5 centimeters (cm) to 4 cm. It is envisioned that body 22 has a length in the range of 3 inches (in) to 7 in from proximal end 26 to a distal end 28.

Body 22 includes a second portion 34 that extends transversely from distal end 28 along an axis b. Second portion 34 extends from first portion 24 in a transverse orientation such that axis b is disposed substantially perpendicular to longitudinal axis a. It is contemplated that second portion 34, disposed along axis b, may be disposed at alternate transverse orientations from first portion 24, relative to longitudinal axis a, for example, perpendicular and/or other angular orientations such as acute or obtuse, co-axial, parallel and/or may be offset or staggered.

Second portion 34 has an arcuate configuration extending between a first end 36 and a second end 38. Second portion 34 defines a cavity, such as, for example, a channel 40 extending from first end 36 to second end 38 such that second portion 34 has a substantially U-shaped cross-section. Channel 40 extends to substantially conform to the arcuate configuration of second portion 34.

It is contemplated that channel 40 can extend a length in a range of 10 cm to 15 cm. It is envisioned that second portion 34 may extend in alternate configurations such as, for example, alternative radius of curvature, linear, offset and/or staggered. It is further envisioned that second portion 34 and/or channel 40 may have alternate cross section configurations such as those alternatives described herein. For example, in one embodiment, second portion 34 has an outside diameter of approximately 1.25 cm and channel 40 is sized to accommodate a 1 cm diameter implant.

Second end 38 includes a tip 39, which has a conical configuration and is tapered to facilitate passage of second portion 34 through tissue and delivery of an implant to a surgical site, as will be discussed. In one embodiment, tip 39 penetrates soft tissue upon disposal at a surgical site. In one embodiment, tip 39 is approximately 40 millimeters (mm) long and tapers to an approximately 2 to 2.5 mm radius nose. It is envisioned that second end 38 may have alternative configurations such as, for example, sharpened, bullet nosed or blunt.

Second portion 34 has a proximal face 42 and channel 40 defines an open distal face 44 of second portion 34. Channel 40 communicates with passageway 32 such that a first member, such as, for example, an expulsion rod 46 extends through passageway 32 and channel 40. Rod 46 includes an axial portion 48 disposed within passageway 32 and a transverse portion 50 disposed within channel 40. It is envisioned that all or only a portion of axial portion 48 and/or transverse portion 50 may have a flexible, semi-rigid or rigid configuration. It is further envisioned that transverse portion 50 defines a distal face that may be planar, arcuate, concave, convex, angled, stepped and/or include a surface configuration such as those described herein.

Rod 46 is disposed within passageway 32/channel 40 and slidably movable relative to body 22 such that rod 46 engages an implant (FIGS. 5-7) disposed in channel 40. Rod 46 is configured to expel the implant from channel 40 through distal face 44 to a surgical site adjacent tissue for treatment thereof, as will be described. It is envisioned that rod 46 may be monolithically formed, integrally connected components or hingedly connected components adjacent the junction of passageway 32 and channel 40. It is further envisioned that rod 46 may have alternate cross section configurations such as those alternatives described herein. It is contemplated rod 46 can deploy an implant from a nested closed position in channel 40 in a range of 10 mm to 20 mm from distal face 44.

Body 22 includes a handle 52, disposed adjacent proximal end 26, configured for manipulation by a medical practitioner during use. Handle 52 has a substantially cylindrical cross-section and an outer surface configured for gripping by a medical practitioner. It is contemplated that handle 52 may have alternative cross-sectional geometries, surface configurations and fastening mechanisms, such as those alternatives described herein.

Handle 52 includes an actuator, such as, for example, a trigger 54 disposed adjacent proximal end 26 and connected to axial portion 48 of rod 46. Trigger 54 includes a depressible button disposed in axial alignment with axial portion 48. Actuation of trigger 54 causes slidable movement of rod 46 within passageway 32/channel 40 relative to body 22 for expulsion of an implant from channel 40. It is envisioned that trigger 54 may be monolithically formed with rod 46 or integrally connected with axial portion 48 via alternative fastening arrangements such as, for example, friction/pressure fit, hinge and/or threaded.

Handle 52 includes a safety element, such as, for example, a lock 53 that includes a protrusion (not shown) that is received by a circumferential groove 55 defined within the outer surface of axial portion 48. Lock 53 is transversely slidable relative to handle 53 via actuation thereof, such that the protrusion is released from groove 55 and implant delivery device 21 is in a non-locked configuration such that the implant can be deployed. A biasing element, for example, a spring (not shown) is disposed with handle 52 to bias the protrusion into groove 55 such that implant delivery device 21 is in a locked configuration and the implant is prevented from being deployed to prevent undesired or inadvertent actuation of trigger 54.

Implant delivery system 20 includes an implant 56 (FIGS. 5-7) configured for disposal in channel 40 and expulsion therefrom via rod 46, as described herein. It is envisioned that implant 56 is loaded with channel 40, delivered to a surgical site including the transverse processes via implant delivery device 21. In one embodiment, implant 56 has a mesh surface 57 that supports at least one biocompatible material and/or agent. See, for example, those implants described in commonly owned U.S. Patent Application Publication No. 20090192474, the contents of which being hereby incorporated by reference herein. It is contemplated that the implant may have alternate configurations, such as, for example, cage, semi-rigid or rigid body, flexible body, interbody and expanding.

It is envisioned that the biocompatible material and/or agent of the implant 56 may include one or more therapeutic agent(s) disposed in one or more layers or homogenously throughout it. For example, implant 56 may include at least one agent including biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as (HA)-TCP, calcium phosphate and calcium sulfite. It is further envisioned that implant 56 may include biologically active agents, for example, biologically active agents coated onto the exterior of implant 56 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

It is envisioned that the agent may include antiviricides; antimicrobials; amino acids; peptides; vitamins; inorganic elements; co-factors for protein synthesis; hormones; living cells such as mesenchymal stem cells, natural extracts, genetically engineered living cells or otherwise modified living cells; DNA delivered by plasmid or viral vectors; tissue transplants; autogenous tissues such as blood, serum, soft, osteoinductive factor; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; amelogenins, growth differentiation factors (e.g., GDF-5) transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; immuno-suppressants; permeation enhancers, e.g., fatty acid esters such as laureate, myristate and stearate monoesters of polyethylene glycol, enamine derivatives, alpha-keto aldehydes, etc.; or nucleic acids.

In various embodiments, to enhance bone growth at the surgical site, implant 56 can include a bone replacement material. Bone replacement materials can include bone particles from fully mineralized bone, demineralized bone particles and combinations thereof. The bone particles can be autograft, allograft, xenogeneic, transgenic bone particles or a combination thereof. In some embodiments, the bone replacement materials include collagen and/or ceramic particles. It is contemplated that the bone replacement materials may include bone cement.

Implant 56 may include one or a plurality of agent reservoirs. The agent reservoirs can be configured as drug depots with medication for pain and may include antibiotics and/or therapeutics. It is envisioned that the agent reservoir contains active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamethoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™) brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

The agent may also include anti-inflammatory agents such as, for example, apazone, celecoxib, diclofenac, diflunisal, enolic acids (piroxicam, meloxicam), etodolac, sulindac, fenamates (mefenamic acid, meclofenamic acid), gold, ibuprofen, indomethacin, ketoprofen, ketorolac, nabumetone, naproxen, nimesulide, salicylates, sulfasalazine[2-hydroxy-5-[-4-[C2-pyridinylamino)sulfonyl]azo]benzoic acid, tepoxalin or tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluocinolone, fluticasone or a combination thereof.

In one embodiment, implant delivery system 20 includes a plurality of implants 56. It is contemplated that employing the plurality of implants 56 can optimize the fusion procedure. The plurality of implants 56 can be variously sized and configured, and/or oriented in a side by side engagement, spaced apart and/or staggered.

Figure 5:
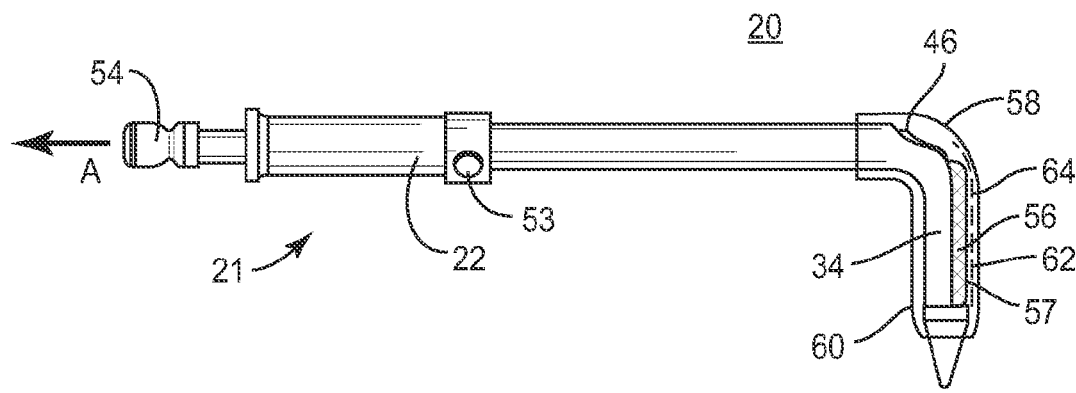
FIG. 5 is a side view of the implant delivery device shown in FIG. 1.
Figure 6:
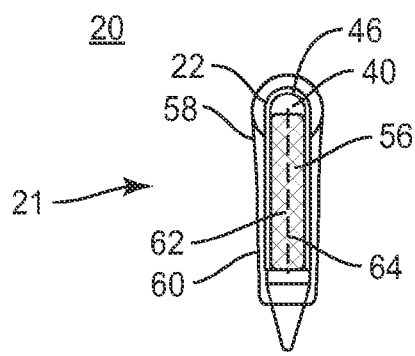
FIG. 6 is a side view of the implant delivery device shown in FIG. 1.
Figure 7:
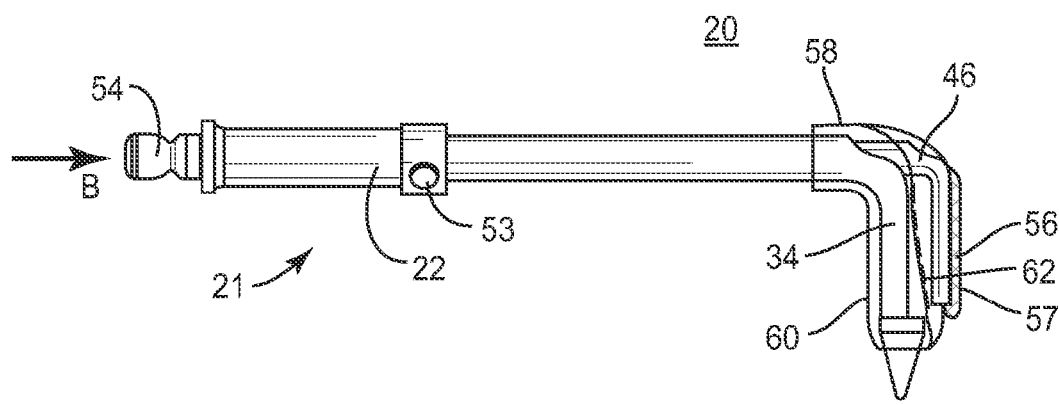
FIG. 7 is a side view of the implant delivery device shown in FIG. 1.

Implant delivery system 20 includes a second member, which is a covering, such as, for example, a sleeve 58, as shown in FIGS. 5-7. Sleeve 58 includes a wall surface 60 disposed about implant 56 disposed in channel 40. Wall surface 60 is oriented in a configuration to define a cylindrical cavity for disposal of second portion 34 and implant 56 disposed within channel 40. It is contemplated that wall surface 60 may be oriented to form alternative cross section configurations such as those described herein. It is further contemplated that all or only a portion of wall surface 60 may be flexible, semi-rigid or rigid.

Wall surface 60 is configured to form an opening 62 for passage of implant 56 therethrough. Wall surface 60 includes a perforated portion 64 that is separable to form opening 62. As rod 46 engages implant 56 to expel implant 56 from channel 40, implant 56 is caused to engage perforated portion 64, which separates and/or fractures adjacent portions of wall surface 60 under such force to create opening 62. Upon formation of opening 62, implant 56 is free to pass through opening 62 for disposal and delivery to a surgical site. It is envisioned that all or only a portion of wall surface 60 may be perforated. It is further envisioned that wall surface 60 may include one or a plurality of openings. It is contemplated that opening 62 may have various geometric configurations such as those alternatives described herein. In one embodiment, wall surface 60 is non-perforated and separates and/or fractures upon engagement of implant 56 therewith. It is contemplated that implant delivery system 20 may be employed without a second member.

In one embodiment, opening 62 is pre formed in wall surface 60 for passage of implant 56 therethrough without separation or fracture of wall surface 60. In one embodiment, the covering is an adhesive film disposed about, for example, wrapped around the outer surface of second portion 34. In one embodiment, wall surface 60 includes an inner surface that includes adhesive and is configured for engagement with an outer surface of second portion 34 such that sleeve 58 is fixed with second portion 34. In one embodiment, the inner surface of wall surface 60 includes adhesive except adjacent to perforated portion 64.

In operation of implant delivery device 21, trigger 54 is set or reset, in the direction shown by arrow A in FIG. 5, such that transverse portion 50 of rod 46 is retracted into channel 40 in a first position, such as, for example, a nested position, as shown in FIG. 5. Implant 56 is disposed and otherwise loaded with channel 40 such that implant 56 is in the nested position.

Sleeve 58 is slidably positioned over implant 56 disposed within channel 40. Sleeve 58 supports implant 56 with channel 40 during delivery to a surgical site and placement of implant 56 with tissue, for example, transverse processes. Implant delivery device 21 with implant 56 supported therewith is delivered to a surgical site, for example, employing minimally invasive or percutaneous techniques.

Upon placement of implant delivery device 21 at the surgical site, lock 53 is manipulated for transverse movement to the unlocked position such that implant 56 can be deployed. Trigger 54 is depressed in the direction shown by arrow B in FIG. 7, to actuate rod 46. Rod 46 is caused to slidably move relative to body 22, in the direction shown by arrow B such that transverse portion 50 extends from channel 40 to a second position, such as, for example, a deployed position, as shown in FIG. 7. Actuation of rod 46 causes transverse portion 50 to forcibly engage implant 56 to expel implant 56 from channel 40 to a deployed position. As implant 56 is expelled from channel 40, implant 56 is caused to engage perforated portion 64, which separates and/or fractures adjacent portions of wall surface 60 under such force to create opening 62.

Upon formation of opening 62, implant 56 passes through opening 62 for placement with the transverse processes. Trigger 54 is reset such that transverse portion 50 retracts back into channel 40. Implant delivery device 21 is removed from the surgical site, leaving implant 56 in place with the transverse processes. In one embodiment, a disposable sleeve 58 is placed about an entire reusable implant delivery device 21 with perforated portion 64 disposed adjacent distal face 44 to form opening 62 for passage of implant 56 therethrough.

In assembly, operation and use, implant delivery system 20, similar to that described above with regard to FIGS. 1-7, is employed, for example, with a surgical procedure on a patient for a fusion or fixation procedure for stabilizing a section of a spine having vertebrae V, which includes vertebra V1, V2 and V3, as shown in FIG. 8. It is envisioned that implant delivery system 20 may be used in any existing surgical method or technique including open surgery, mini-open surgery, minimally invasive surgery and percutaneous surgical implantation. The components of implant delivery system 20 can be delivered or implanted as a pre-assembled device or can be assembled in situ. The components of implant delivery system 20 may be completely or partially revised, removed or replaced in situ. In one embodiment, implant delivery system 20 is employed with a procedure to supplement or to be used in association with an interbody fusion, which may be performed in a prior, concurrent or subsequent procedure. The components of implant delivery system 20 are employed to deliver an implant to a surgical site to provide support and maximize stabilization of vertebrae V.

A method for treatment of vertebrae V employing implant delivery system 20, in accordance with the principles of the present disclosure, includes a posterolateral fusion procedure.

In one embodiment, a surgeon employs a minimally invasive technique and makes an incision in the skin of a patient over and in approximate alignment with a surgical site, which includes vertebrae V. Implant delivery system 20 includes a dilator (not shown) employed to separate the muscles and tissues to create a passageway along a desired trajectory, such as those described above, to the surgical site through which the surgery may be performed. It is contemplated that the dilator may include one or a plurality of dilators, and/or employ a retractor, to gradually separate muscle and tissue to create a portal including the passageway. It is further contemplated that the dilator may be configured as an in-situ guidance instrument and may include an endoscope camera tip. Implant delivery system 20 includes a retractor (not shown) positioned and docked adjacent the surgical site over the incision.

Figure 9:
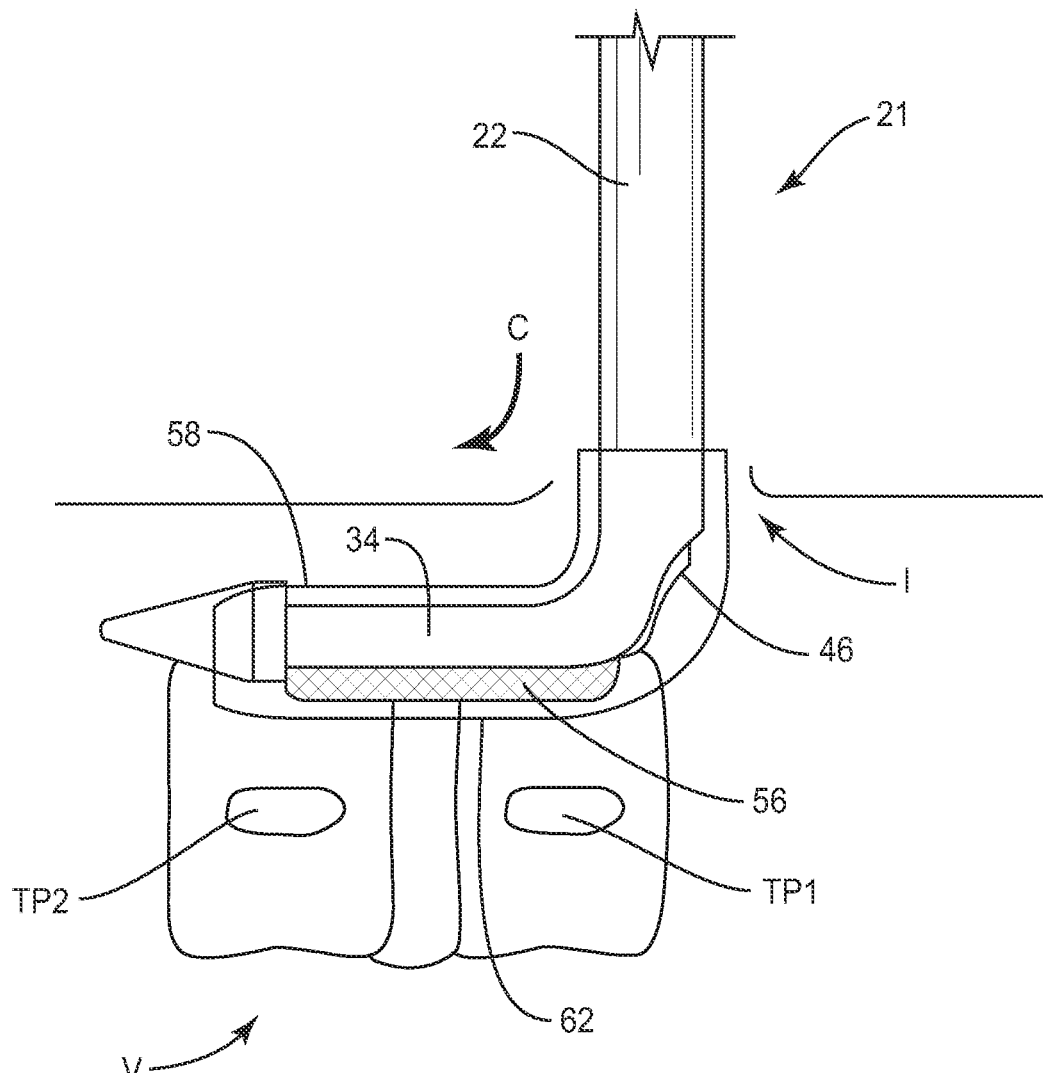
FIG. 9 is a side, cropped view of the section of the spine shown in FIG. 8 and a side, cropped view of an implant delivery system in accordance with the principals of the present disclosure.

In one embodiment, the surgeon employs a percutaneous technique, as shown in FIG. 9. For example, the surgeon makes a small incision I in the skin of a patient over and in approximate alignment with the surgical site, which includes vertebrae V. A dilator (not shown) may be used that includes a cannula, mini-open retractor or tube, which creates and defines a passageway for passage of the components of implant delivery system 20, discussed herein, to the surgical site from a desired trajectory.

Upon establishment of the passageway for the method of the posterolateral fusion, a preparation instrument(s) (not shown) is inserted within the passageway and disposed adjacent transverse processes TP1, TP2 of vertebrae V. For example, a preparation instrument, such as a Cobb elevator, a surgical drill and/or a sleeved burr is disposed in the passageway and adjacent transverse processes TP1, TP2 at the surgical site. The preparation instrument, with the assistance of image guidance, decorticates transverse processes TP1, TP2. It is envisioned that the preparation instrument(s) may include rasps, curettes and/or a rotating tissue remover such as a rapid disc removal system that can be low profile to cut and remove disc and/or bone material simultaneously. The preparation instrument(s) is employed to remove tissue and fluids adjacent tissues and/or bone, scrape and/or remove tissue from vertebral surfaces, as well as aspirate and irrigate the region according to the requirements of a particular surgical application. The preparation instrument is removed from the passageway thereafter.

Figure 10:
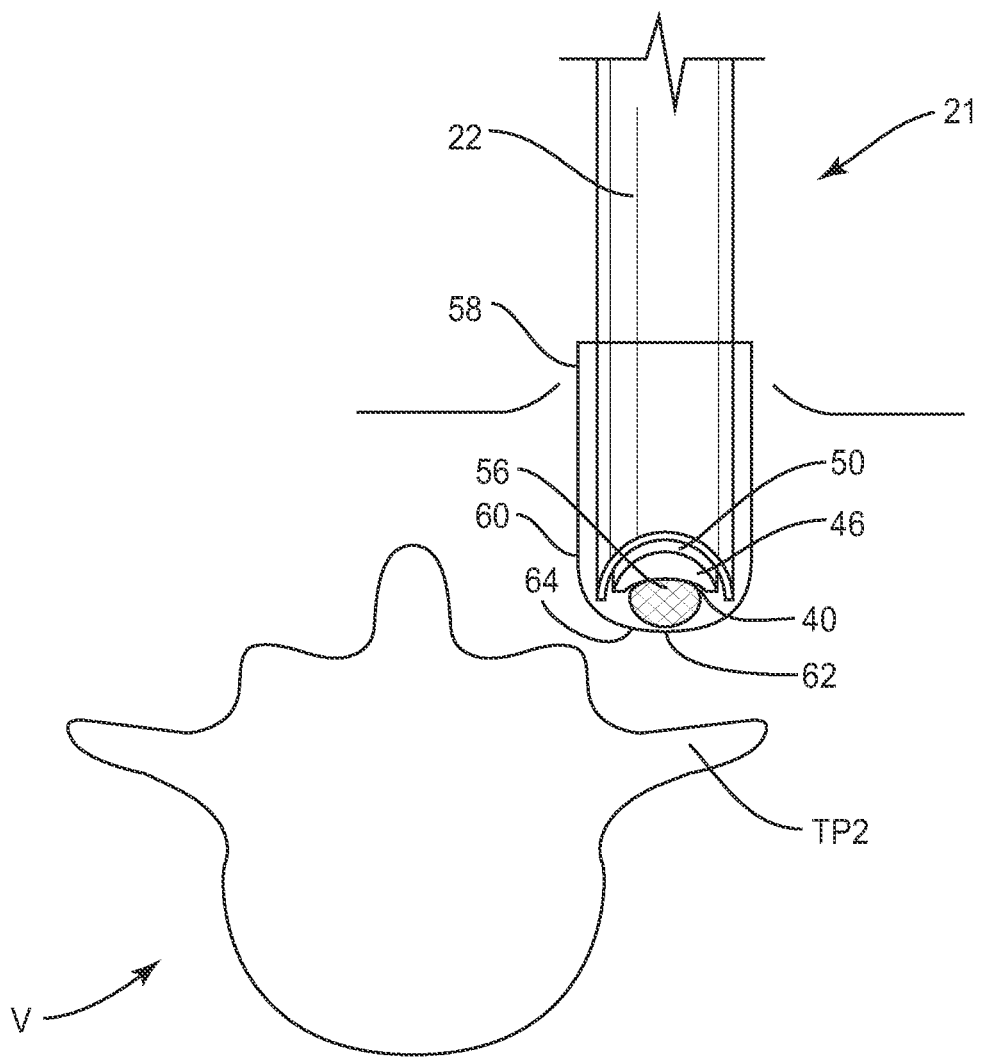
FIG. 10 is an axial view of the spine section and the implant delivery system shown in FIG. 9.

Implant delivery device 21 is provided for delivering implant 56 to the surgical site. Trigger 54 (FIG. 5) is set or reset such that transverse portion 50 of rod 46 is retracted into channel 40 in the nested position, as shown in FIGS. 9-10. Implant 56 is loaded with channel 40 such that implant 56 is in the nested position.

Sleeve 58 is slidably positioned over implant 56 disposed within channel 40. Sleeve 58 supports implant 56 with channel 40 during delivery to a surgical site and placement of implant 56 adjacent transverse processes TP1, TP2. Implant delivery device 21 is inserted through incision I within the passageway using an arc like motion, in the direction shown by arrow C in FIG. 9, to deliver implant 56 to the surgical site adjacent transverse processes TP1, TP2 for the arthrodesis treatment of vertebrae V.

Figure 11:
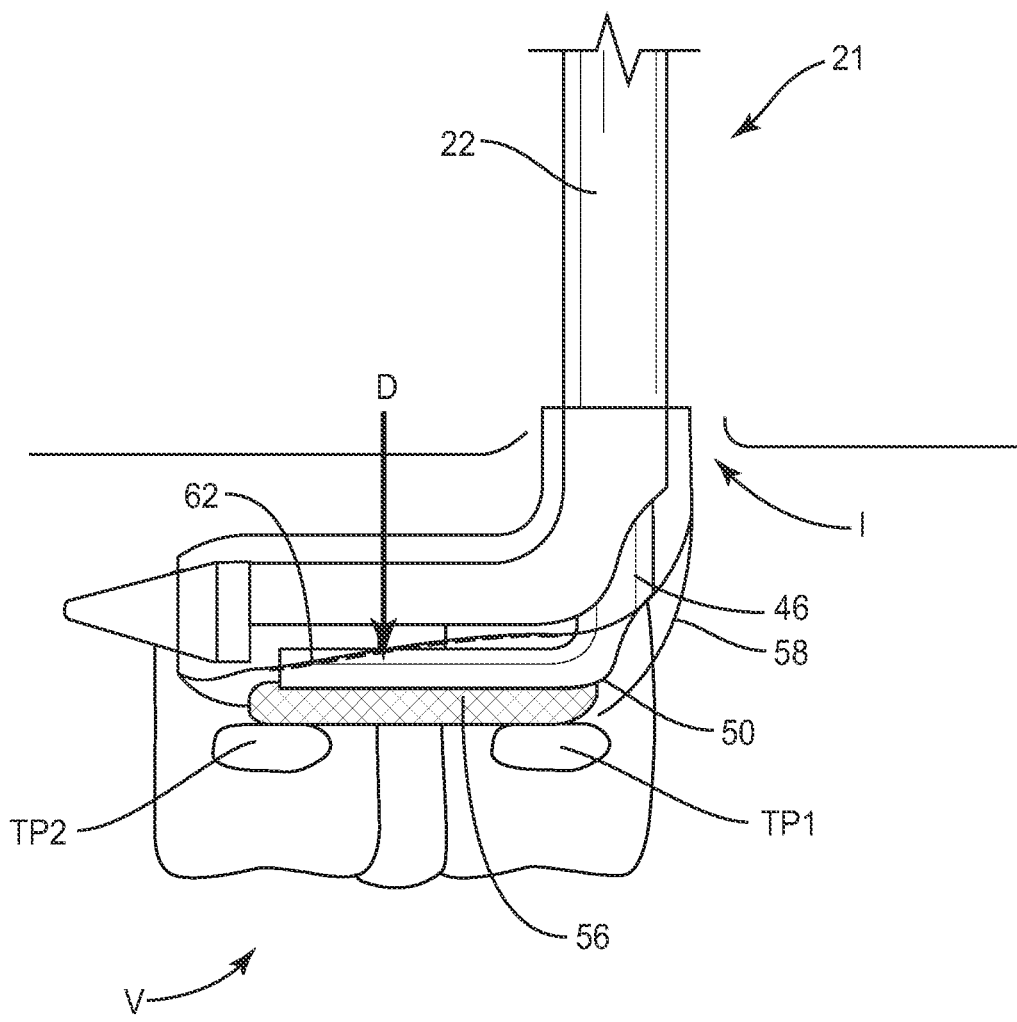
FIG. 11 is a side view of the spine section and the implant delivery system shown in FIG. 9.

Upon placement of second portion 34 adjacent transverse processes TP1, TP2, trigger 54 is depressed to actuate rod 46. Rod 46 is caused to slidably move relative to body 22 such that transverse portion 50 extends from channel 40 to the deployed position, as shown in FIG. 11. Actuation of rod 46 causes transverse portion 50 to forcibly engage implant 56 to expel implant 56 from channel 40 to a deployed position. As implant 56 is expelled from channel 40, implant 56 is caused to engage perforated portion 64, which separates and/or fractures adjacent portions of wall surface 60 under such force to create opening 62. Upon formation of opening 62, implant 56 passes through opening 62, as shown by arrow D in FIG. 11, for placement with transverse processes TP1, TP2. Deployment of implant 56 causes implant 56 to engage and pack upon transverse processes TP1, TP2. It is envisioned that image guidance and/or tactile response from implant delivery device 21 provide indication that implant 56 is desirably positioned with transverse processes TP1, TP2. It is contemplated that the configuration of the components of implant delivery system 20 advantageously prevent undesired interference and/or engagement with soft tissues adjacent the surgical site.

Figure 12:
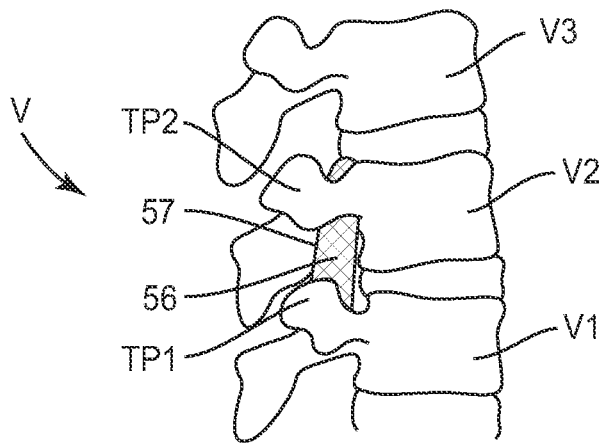
FIG. 12 is a perspective view of the spine section shown in FIG. 8 and one embodiment of an implant of the system in accordance with the principles of the present disclosure.

Trigger 54 is reset such that transverse portion 50 retracts into channel 40. Implant delivery device 21 is removed from the surgical site, leaving implant 56 in place with transverse processes TP1, TP2, as shown in FIG. 12. It is envisioned that image guidance, concurrent and/or subsequent to the fusion procedure, can verify desired placement of implant 56 with transverse processes TP1, TP2. It is further envisioned that osteogenic material(s), similar to those described herein, may be disposed and/or packed at the surgical site adjacent implant 56 and transverse processes TP1, TP2.

In one embodiment, implant delivery system 20 may include fastening elements, which may include locking structure, to be used with implant 56 and configured for fixation with surfaces of vertebrae V to secure implant 56 and provide complementary stabilization and immobilization to vertebrae V. It is envisioned that locking structure may include fastening elements such as, for example, clips, hooks, adhesives and/or flanges. It is envisioned that implant delivery system 20 can be used with screws and/or rods to enhance fixation. It is contemplated that implant delivery system 20 and any screws and attachments may be coated with an osteoconductive material such as those described herein for enhanced bony fixation to the treated area. The components of implant delivery system 20 can be made of radiolucent materials such as polymers. Radiomarkers may be included for identification under x-ray, fluoroscopy, CT or other imaging techniques.

It is envisioned that the use of microsurgical and image guided technologies may be employed to access, view and repair spinal deterioration or damage, with the aid of implant delivery system 20. Upon completion of the procedure, the surgical instruments and assemblies are removed and the incision is closed.

Implant delivery system 20 may be employed for performing spinal surgeries, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 13:
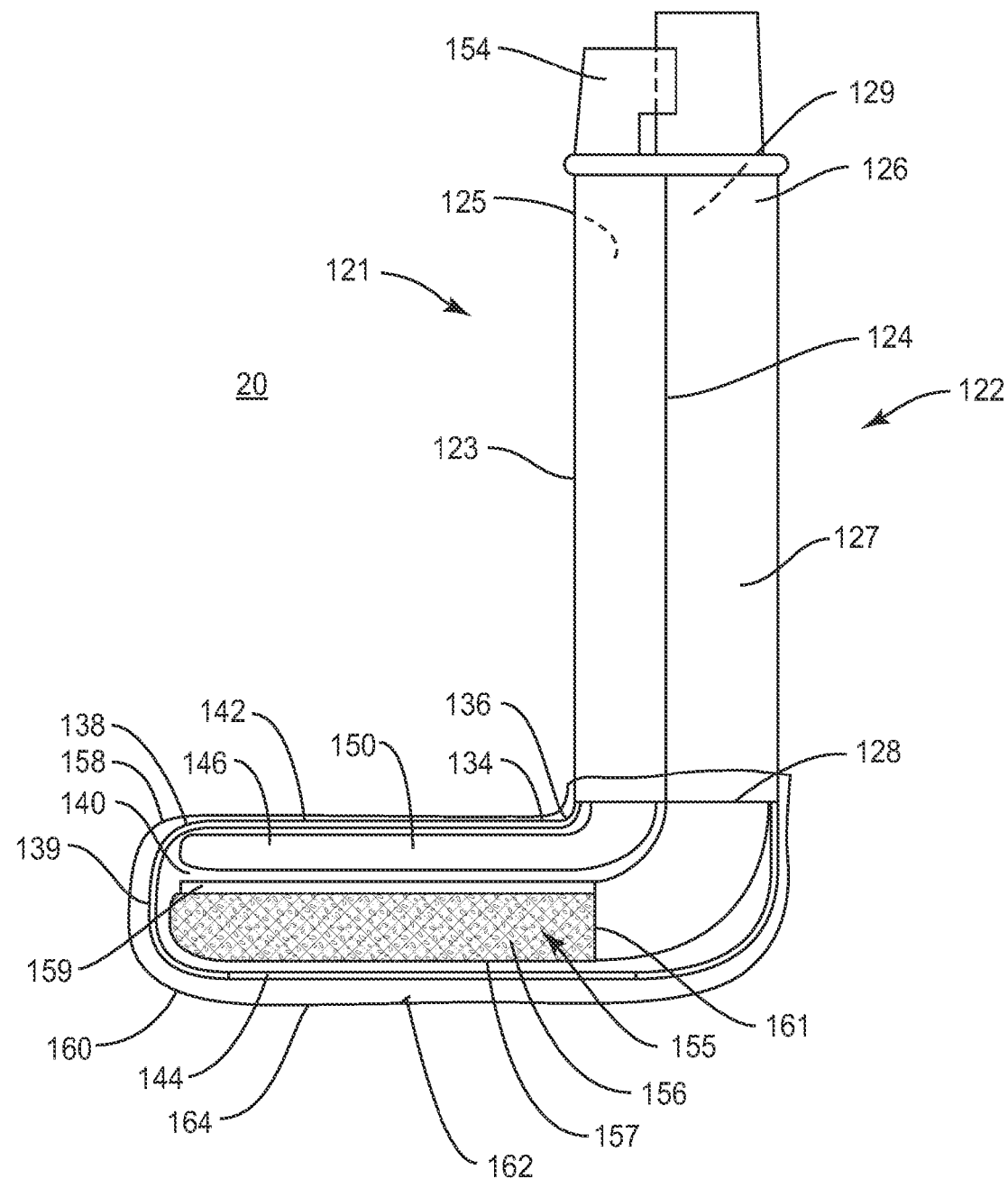
FIG. 13 is a perspective view of one embodiment of an implant delivery system in accordance with the principles of the present disclosure.

In one embodiment, as shown in FIG. 13, similar to implant delivery system 20 described above with regard to FIGS. 1-12, system 20 includes an implant delivery device 121. Implant delivery device 121 includes a body 122 having a first portion 124 that extends from a proximal end 126 to a distal end 128 along a longitudinal axis of body 122. Body 122 is configured for disposal within a body cavity to deliver an implant to a surgical site.

First portion 124 includes a first housing 123, which defines an inner cavity, such as, for example, a first passageway 125 and a second funnel housing 127, which defines an inner cavity, such as, for example, a second passageway 129. Body 122 includes a second portion 134 that extends transversely from distal end 128, similar to second portion 34 described above. Second portion 134 defines a cavity, such as, for example, a channel 140 extending from a first end 136 to a second end 138 such that second portion 134 has a substantially U-shaped cross-section. Channel 140 extends to substantially conform to the configuration of second portion 134.

Second end 138 includes a tip 139 that facilitates passage of second portion 134 through tissue and delivery of an implant to a surgical site. Second portion 134 has a proximal face 142 and channel 140 defines an open distal face 144 of second portion 134. Channel 140 communicates with passageway 125 such that a first member, such as, for example, an expulsion rod 146 extends through passageway 125 and channel 140. Rod 146 includes an axial portion (not shown) disposed within passageway 125 and a transverse portion 150 disposed within channel 140.

Rod 146 is disposed within passageway 125/channel 140 and slidably movable relative to body 122 such that rod 146 engages an implant disposed in channel 140. Rod 146 is configured to expel the implant from channel 140 through distal face 144 to a surgical site adjacent tissue for treatment thereof, as will be described.

Rod 146 includes an actuator 154 disposed adjacent proximal end 126 and connected to the axial portion of rod 146. Actuator 154 causes slidable movement of rod 146 within passageway 125/channel 140 relative to body 122 for expulsion of an implant from channel 140.

Channel 140 also communicates with passageway 129. Passageway 129 is configured to deliver at least one biocompatible material and/or agent 155, similar to those described herein, to form an implant 156 of implant delivery system 20. Implant 156 has a mesh surface 157 that defines an inner cavity. Implant 156 is configured for disposal in channel 140 and expulsion therefrom via rod 146. An evacuated implant 156 is loaded with channel 140 and removably mounted with a post 159 that maintains an opening 161 of implant 156 in an open position for receiving material and/or agent 155. Material and/or agent 155 is delivered via funnel 127 to the inner cavity of evacuated implant 156 through opening 161. Implant 156, which includes material and/or agent 155, is released from post 159 via manipulation by a practitioner and/or retraction of post 159, and delivered to a surgical site including the transverse processes via implant delivery device 121, similar to that described above.

Implant delivery system 20 includes a second member, such as, for example, a sleeve 158, similar to sleeve 58 described above. Sleeve 158 includes a wall surface 160 disposed about implant 156 disposed in channel 140. Wall surface 160 is oriented in a configuration to define a cylindrical cavity for disposal of second portion 134 and implant 156 disposed within channel 140. Wall surface 160 is configured to form an opening 162 for passage of implant 156 therethrough. Wall surface 160 includes a perforated portion 164 that is separable to form opening 162. As rod 146 engages implant 156 to expel implant 156 from channel 140, implant 156 is caused to engage perforated portion 164, which separates and/or fractures adjacent portions of wall surface 160 under such force to create opening 162. Upon formation of opening 162, implant 156 is free to pass through opening 162 for disposal and delivery to a surgical site.

In operation of implant delivery device 121, similar to operation and the method of treatment employing implant delivery device 21 described above, transverse portion 150 of rod 146 is retracted into channel 140 in a nested position. Evacuated implant 156 is disposed and otherwise loaded with channel 140 and removably mounted with post 159 that maintains opening 161 in an open position for receiving material and/or agent 155. Material and/or agent 155 is delivered via funnel 127 to the inner cavity of evacuated implant 156 through opening 161.

Sleeve 158 is slidably positioned over implant 156 disposed within channel 140. Sleeve 158 supports implant 156 with channel 140 during delivery to a surgical site and placement of implant 156 with transverse processes. Implant delivery device 121 with implant 156 supported therewith is delivered to a surgical site, for example, employing minimally invasive or percutaneous techniques.

Upon placement of implant delivery device 121 at the surgical site, actuator 154 is depressed to actuate rod 146. Rod 146 is caused to slidably move relative to body 122 such that transverse portion 150 extends from channel 140 to a deployed position, similar to that described above. Actuation of rod 146 causes transverse portion 150 to forcibly engage implant 156 to expel implant 156 from channel 140 to a deployed position. As implant 156 is expelled from channel 140 and released from post 159, implant 156 is caused to engage perforated portion 164, which separates and/or fractures adjacent portions of wall surface 160 under such force to create opening 162.

Upon formation of opening 162, implant 156 passes through opening 162 for placement with the transverse processes. Implant delivery device 121 is removed from the surgical site, leaving implant 156 in place with the transverse processes.

Figure 14:
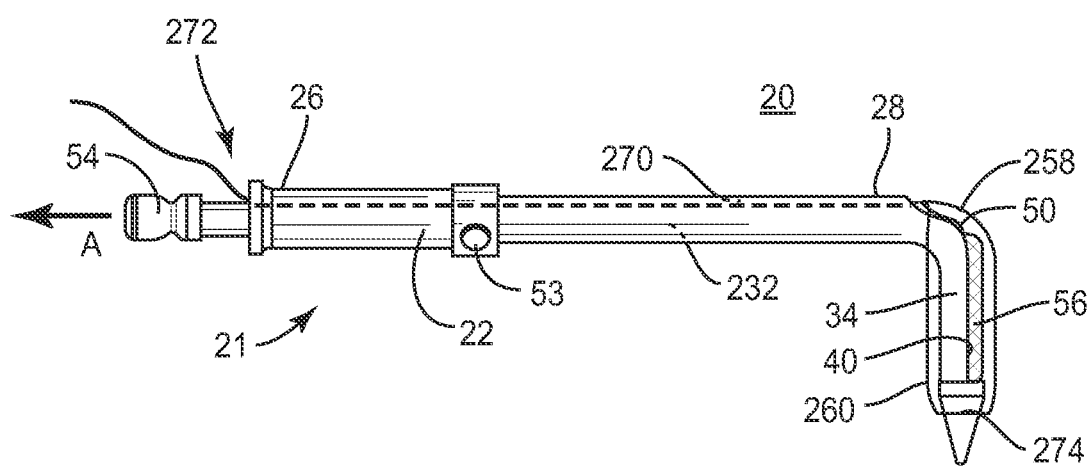
FIG. 14 is a perspective view of one embodiment of an implant delivery system in accordance with the principles of the present disclosure.

In one embodiment, as shown in FIG. 14, similar to implant delivery system 20 described above with regard to FIGS. 1-12, body 22 includes a passageway 232, similar to passageway 32 described above, and a lumen 270 (shown in phantom) that extends between proximal end 26 and distal end 28. Lumen 270 is configured for slidable movement of a line or wire 272 that is connected to a sleeve 258, similar to sleeve 58 described above. Sleeve 258 has a solid wall surface 260 and a distal opening 274.

Prior to expulsion of implant 56 from channel 40, as described above, a proximal end of wire 272 is manipulated in the direction of arrow A to remove sleeve 258 from the surgical site. As wire 272 is drawn, sleeve 258 has a flexible configuration and is slidably moved over second portion 34 such that implant 56, transverse portion 50 and second portion 34 pass through distal opening 274, which expands as the components slide therethrough. As sleeve 258 uncovers second portion 34 and implant 56, sleeve 258 is drawn through lumen 270 via the connection with wire 272 and removed from body 22 through proximal end 26. Implant 56 is exposed and delivered to the surgical site as described above.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant delivery device comprising:
 a body having a first portion and a first transverse portion defining a cavity in at least a portion thereof, the first transverse portion having an open distal face;
 a first member having an elongated body, a second transverse portion disposed on the open distal face of the first transverse portion, the second transverse portion corresponding to the first transverse portion and configured to fit within the first transverse portion such that the second transverse portion is partially enclosed by the first transverse portion of the body, the first member having at least a portion thereof disposable in the cavity and movable relative to the first transverse portion; and
 a second member having a surface disposed about an implant disposable in the cavity, the surface including an opening,
 wherein the first member is engageable with the implant to expel the implant from the cavity and through the opening.

2. The implant delivery device of claim 1, wherein the first portion defines a longitudinal axis and the first transverse portion extends transversely from a distal end of the first portion.

3. The implant delivery device of claim 1, wherein the first portion defines a cavity that communicates with the cavity of the first transverse portion such that the first member extends through the cavities of the first portion and first transverse portion.

4. The implant delivery device of claim 1, wherein the first member includes an actuator disposed adjacent a proximal end of the first portion.

5. The implant delivery device of claim 1, wherein the first transverse portion has an arcuate configuration.

6. The implant delivery device of claim 1, wherein the cavity of the first transverse portion has a channel configuration.

7. The implant delivery device of claim 1, wherein the second member is a sleeve.

8. The implant delivery device of claim 1, wherein the surface includes a perforation that forms the opening.

9. An implant delivery system comprising:
   an elongated body having an elongated channel, extending from a proximal end to a distal end along a longitudinal axis of the body, the proximal end including a handle,
   a first transverse portion extending transversely from the distal end of the elongated body, the first transverse portion having an open distal face;
   a rod being movable relative to the body, the rod including an axial portion disposable within the body and a second transverse portion disposed on the open distal face of the first transverse portion, the second transverse portion corresponding to the first transverse portion and configured to fit within the first transverse portion of the body such that the second transverse portion is partially enclosed by the first transverse portion of the body;
   an implant disposable in the channel; and
   a covering defining a surface disposed about at least a portion of the implant disposed in the channel, the surface being configured to form an opening,
   wherein the rod is engageable with the implant in the channel to expel the implant from the channel through the opening.

10. The implant delivery system of claim 9, further comprising an actuator connected to the rod and disposed adjacent the handle.

11. The implant delivery system of claim 10, wherein the actuator is a depressible button disposed in axial alignment with the axial portion of the rod.

12. The implant delivery system of claim 9, wherein the covering is a sleeve.

13. The implant delivery system of claim 9, wherein the surface includes a perforation that forms the opening.

14. The implant delivery system of claim 9, wherein the implant has a mesh surface that supports at least one biocompatible material.

\* \* \* \* \*